United States Patent [19] [11] 4,009,963
George [45] Mar. 1, 1977

[54] ARRANGEMENT FOR PRODUCING FREE ATOMS OF A SUBSTANCE FOR ATOMIC SPECTROSCOPY PURPOSES

[75] Inventor: Richard Alexander George, Eindhoven, Netherlands

[73] Assignee: U.S. Philips Corporation, New York, N.Y.

[22] Filed: Mar. 19, 1975

[21] Appl. No.: 559,824

[30] Foreign Application Priority Data
Mar. 25, 1974 Netherlands ............... 7403968

[52] U.S. Cl. .................. 356/85; 356/244
[51] Int. Cl.² ..................... G01J 3/30
[58] Field of Search ............. 356/85, 244

[56] References Cited
UNITED STATES PATENTS
3,817,629 6/1974 Witte ................... 356/85
3,819,279 6/1974 Braun et al. .......... 356/244
3,893,769 7/1975 Woolley .............. 356/244

*Primary Examiner*—Vincent P. McGraw
*Attorney, Agent, or Firm*—Frank R. Trifari; Leon Nigohosian

[57] ABSTRACT

An arrangement is discussed for producing free atoms of a substance for atomic spectroscopy purposes comprising an oven and an oven element, which contains the substance to be examined, which oven is surrounded by cooling means which, during the spectroscopic measurements, cool the oven wall and which must have a temperature of at least 30° C.

2 Claims, 1 Drawing Figure

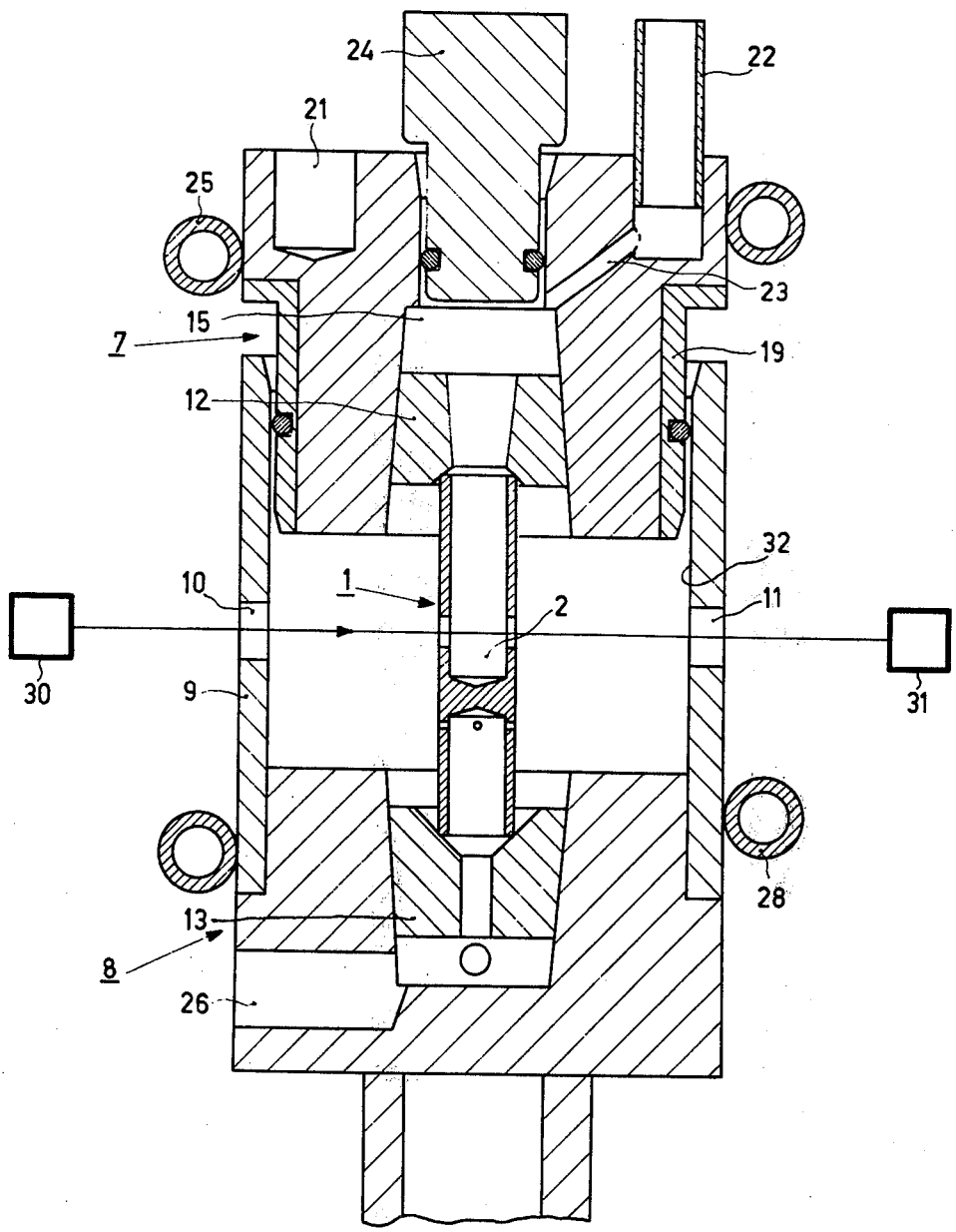

ARRANGEMENT FOR PRODUCING FREE ATOMS OF A SUBSTANCE FOR ATOMIC SPECTROSCOPY PURPOSES

The invention relates to an arrangement for producing free atoms of a substance for atomic spectroscopy purposes, and more in particular to the use of an oven and an oven element for the production of free atoms of a sample in for example an atomic absorption or atomic fluorescence spectrophotometer.

An arrangement of the above-mentioned type, which employs a graphite oven element which contains the sample is known from German Patent Specification No. 2,023,336. It has been found that a graphite oven element, for example an element in the form of a crucible has several advantages compared with a flame used for the same purposes. First of all, the absolute detection limits for a graphite crucible to be heated electrically are lower than for a flame. Secondly, a crucible allows very small volumes to be analyzed. In the third place a sample can be analyzed directly without previous storage or chemical treatment.

In practice it has been found that the use of a graphite crucible without specific precautions has some drawbacks.

One of said drawbacks is the oxidation to which the graphite is subject at high temperatures. Oxidation is prevented by enclosing the crucible in an oven and feeding an inert gas past the crucible.

Another drawback is that the crucible is affected by water vapour which escapes from the sample when it is heated in the crucible. The crucible is readily attacked by said water vapour which reacts with graphite, so that after a comparatively low number of spectrochemical analyses the crucible will break.

A further drawback is that owing to the reaction of water vapour with graphite dust is produced which adversely affects the stability of the measuring signal and which, moreover, settles at the oven wall, so that the radiation beam which must interact with the free atoms of the sample is partly absorbed by said graphite dust.

It is an object of the invention to eliminate the last-mentioned drawback.

An arrangement for the production of free atoms of a substance for the purpose of atomic spectroscopy, which comprises an oven and an oven element which contains the substance to be examined, which oven is surrounded by cooling means which during the spectroscopic measurements cool the oven wall, is therefore characterized in that the cooling means have a temperature of at least 30° C.

The invention is based on the following recognition.

Assume that the mass of the water in the sample is $m$ and the oven volume V. If all the water would evaporate, the density $\rho$ of the water vapour would equal $m/V$. At a temperature T of the oven wall the vapour cannot exceed a critical density $\rho_{cT}$. In general, $m/V >> \rho_{cT}$.

The water vapour is carried off by the inert carrier gas which has a volume velocity L (per second a gas volume L is displaced). The inert carrier gas cannot contain any water vapour with density greater than $\rho_{cT}$. The maximum amount of water vapour which is carried off by the inert carrier gas per second is $\rho_{cT}.L$. During the drying phase which lasts $t$ seconds a maximum amount of $\rho_{cT}Lt$ is carried off. Said amount is smaller than $m$, so that a part of the water vapour from the sample deposits on the cold oven wall. During the phase in which the sample disintegrates into atoms, i.e. at a high temperature of the crucible and the sample, said condensed water vapour will evaporate again owing to the heat omitted by the crucible. Said re-evaporated water vapour reacts with the graphite.

By increasing the temperature of the oven wall the critical density $\rho_{cT}$ increases substantially (almost exponentially), so that the product $\rho_{cT}Lt$ increases substantially and exceeds $m$. Condensation on the oven wall no longer occurs.

The invention will be described by way of example with reference to the drawing, which shows an arrangement according to the invention.

In the drawing the sole FIGURE shows an oven which is suited for use in a spectrophotometer for atomic absorption. In the centre of the oven the graphite crucible 1 is disposed. The crucible 1 has a cavity 2 which contains the substance to be examined. The graphite crucible 1 is enclosed between annular graphite holders 12 and 13, which form part of the electrodes 7 and 8 respectively. The electrodes 7 and 8 have a high electrical conductivity and a low contact resistance with respect to the holders 12 and 13. The electrode 7 is a sliding fit in the oven wall 9, so that said electrode and the crucible 1 can readily be removed. The electrode 8 is integral with the oven wall 9.

In the recess 21 of the electrode 7 and in the recess 26 of the electrode 8 electrical leads are fitted which can be connected to a voltage source (not shown). A current of an inert gas is fed to the centre of the oven via the pipe 22 and the passage 23 in the electrode 7. Via the openings 10 and 11 in the oven wall 9 the gas leaves the oven.

The central hole in the electrode 7 is closed by a removable plug 24.

During operation the crucible 1 is heated in consecutive temperature ranges by the current derived from the voltage source. Eventually, the temperature is so high that the substance to be examined in the cavity 2 of the crucible 1 disintegrates into free atoms. In this phase a radiation beam from the radiation source 30 is passed via the holes 10 and 11 in the oven wall 9 to the detector 31. From the degree of absorption of the radiation beam data can be derived about the composition of the substance to be examined in the cavity 2 of the crucible 1.

During operation the oven wall is continuously cooled. This is effected by passing cooling water through the spiral tube which surrounds the oven wall, of which tube the coils 25 and 26 are shown. According to the invention the temperature of the cooling water is selected so, for example 30° C, that no water vapor condenses on the inner side 32 of the wall 9. It appears that the active lifetime of the crucible 1 is now substantially longer, for example 10 times longer, than in the case that the temperature of the cooling water has the normal value of approximately 10° C.

What is claimed is:

1. An apparatus for producing free atoms of a substance for atomic spectroscopy purposes, comprising an oven and an oven element that contains said substance, said apparatus further comprising cooling means adapted to maintain said oven at a temperature level such that there exists therein the situation where $$\rho_{cT}Lt > m,$$

$\rho_{cT}$ is the critical water vapor density,
L is the volume velocity of a carrier gas through said oven,
$t$ is the duration of the drying phase for said oven, and
$m$ is the mass of the water in said oven.

2. An apparatus as recited in claim 1, wherein said cooling means surrounds said oven and cools the wall of said oven during the spectroscopic measurements, said cooling means have a temperature of at least 30° C.

* * * * *